(12) United States Patent
Vecht

(10) Patent No.: US 10,175,171 B2
(45) Date of Patent: Jan. 8, 2019

(54) COMPACT MULTI-UV-LED PROBE SYSTEM AND METHODS OF USE THEREOF

(71) Applicant: Aron Vecht, London (GB)

(72) Inventor: Aron Vecht, London (GB)

( * ) Notice: Subject to any disclaimer, the term of this patent is extended or adjusted under 35 U.S.C. 154(b) by 0 days.

(21) Appl. No.: 15/748,197

(22) PCT Filed: Jul. 28, 2016

(86) PCT No.: PCT/IL2016/050826
§ 371 (c)(1),
(2) Date: Jan. 29, 2018

(87) PCT Pub. No.: WO2017/021952
PCT Pub. Date: Feb. 9, 2017

(65) Prior Publication Data
US 2018/0217063 A1 Aug. 2, 2018

Related U.S. Application Data

(60) Provisional application No. 62/200,003, filed on Aug. 1, 2015.

(51) Int. Cl.
*G01N 21/64* (2006.01)
*G01J 3/02* (2006.01)

(52) U.S. Cl.
CPC .......... *G01N 21/645* (2013.01); *G01J 3/0218* (2013.01); *G01N 2021/6419* (2013.01);
(Continued)

(58) Field of Classification Search
CPC ......... G01N 21/645; G01N 2021/6419; G01N 2021/0221; G01N 2201/062; G01J 3/0218
See application file for complete search history.

(56) References Cited

U.S. PATENT DOCUMENTS

| 6,110,106 A * | 8/2000 | MacKinnon et al. ...................... A61B 5/0071 600/160 |
| 2011/0117025 A1* | 5/2011 | Dacosta ............... A61B 5/0059 424/9.6 |
| 2012/0245473 A1 | 9/2012 | Mycek et al. |

FOREIGN PATENT DOCUMENTS

| WO | 9937204 A1 | 7/1999 |
| WO | 9966830 A1 | 12/1999 |

(Continued)

OTHER PUBLICATIONS

Written Opinion of the International Searching Authority, dated Nov. 15, 2016.

*Primary Examiner* — David Porta
*Assistant Examiner* — Faye Boosalis
(74) *Attorney, Agent, or Firm* — Eva Leah Taksel

(57) ABSTRACT

The present invention provides a multi UV-LED probe system for detection of a characteristic of a sample, the system including a device comprising a probe head, the probe head including a plurality of UV-LEDs, an optic fiber bundle, an optional heating surface, an optional cooling surface and a light directing means adapted to transfer UV from the plurality of UV-LEDs to a region of the sample and further adapted to receive fluorescent light from the region to focus it into the optic fiber bundle and a power source adapted to provide electrical energy to the plurality of UV-LEDs, a spectrophotometer configured to receive the fluorescent light from the optic fiber bundle and a processor adapted to receive signals associated with the fluorescent light and to process the signals to provide the detection of the characteristic of the sample.

23 Claims, 4 Drawing Sheets

(52) U.S. Cl.
CPC .......... *G01N 2021/6421* (2013.01); *G01N 2021/6476* (2013.01); *G01N 2201/0221* (2013.01); *G01N 2201/062* (2013.01)

(56) References Cited

FOREIGN PATENT DOCUMENTS

| WO | 2005032361 A2 | 4/2005 |
| --- | --- | --- |
| WO | 2008124542 A1 | 10/2008 |
| WO | 2014184337 A1 | 11/2014 |

\* cited by examiner

COMPACT MULTI-UV-LED PROBE SYSTEM AND METHODS OF USE THEREOF

FIELD OF THE INVENTION

The present invention relates generally to UV-LED apparatus and methods, and more specifically to methods and apparatus for simultaneous multi-wavelength UV-LED probe systems and methods of use thereof.

BACKGROUND OF THE INVENTION

Traditionally, UV fluorescence spectroscopy is conducted using a single UV source and a mechanically swept sensor for measuring the emitted light. Recently, many new low-cost UV-emitting LEDs have emerged, offering a broad variety of wavelengths ranging from about 280 nm up to and including visible blue light.

Some patent publications in the field include WO04070369A1, which relates to a method for determining and/or monitoring impurity states in different fluids by using crystalline inorganic semi-conductor diodes (LED) emitting a white light and injection light-emitting diodes emitting at least one infrared radiation (RED) and/or ultra violet radiation (UVED). The method uses, in particular, the modification of the emission spectrum of the white LED. Variations in the peak wave lengths, in the ratios of the peaks of the light-emitting injection in relation to the peak of the photoluminescence, in selective absorptions, in excitations on the fluorescence, in intensities of the peak wave lengths and in integral emissions are used in addition to comparison of data to the modified spectrum of the infrared emitter and/or the UV emitter. The variations are registered with the help of a fiber optic compact spectrometer or a similar receiver. This method is automatically calibrated if the ratio of the injection luminescence to the photoluminescence of the white LED for similar flowing current densities represents a diode specific constant. Exceptionally reliable economical sensors are produced and constructed in a fast manner according to said method and can be used in many methods associated with fluids, for example, in cleaning processes and chemical technology.

US2006192957A discloses a spectrophotometer for integration purposes, including a measurement head with an illumination arrangement including at least one light source for the illumination of a measurement object located in a measurement plane (M) under an angle of incidence of at least 45 degrees, with a pick-up arrangement for capturing the measurement light remitted by the measurement object under an angle of reflection of the essentially 0 degrees relative to the perpendicular of the measurement plane, a spectrometer arrangement with an entry slot for the spectral splitting of the measurement light received through the entry slot and captured and with a photoelectric receiver arrangement exposed to the spectrally split measurement light for conversion of the individual spectral portions of the measurement light into corresponding electrical signals.

It further includes an electronic control, which controls the light source and produces digital measurement values from the electrical signals generated by the photoelectric receiver arrangement. The light source is constructed as a flat cosine radiator and is positioned in such a way that its radiation lobe is essentially perpendicular to the measurement plane (M) and the distance of the light source from the optical axis of the pick-up arrangement is essentially the same as the distance of the light source from the measurement plane.

US2012001094A describes an apparatus for measuring fluorescence of potable liquids contained within an optical quartz cell includes a deep UV laser or a compact UV LED that generates a light beam. A UV blocking and visible light transmitting optical filter reduces out-of-band emission from the LED. The optical quartz cell is between a pair of plane mirrors so that light from the light source travels through it several times. A concave mirror collects a fluorescence signal and has a common optical axis with a lens. The common optical axis is normal to an optical axis of the light beam. The concave mirror and lenses are positioned on opposite sides of the optical quartz cell. A fluorescence detector is in optical alignment with the concave mirror and the lens. Optical wavelength selection of the fluorescence emission uses optical filters or a spectrometer.

There is still a need to provide improved optical detection systems and methods.

SUMMARY OF THE INVENTION

It is an object of some aspects of the present invention to provide improved optical detection systems and methods.

In some embodiments of the present invention, improved methods and apparatus are provided for detecting an entity using multi-UV-LEDs.

In some further embodiments of the present invention, improved methods and apparatus are provided for detecting an entity using multi-UV-LEDs in combination with a heating/cooling apparatus.

In other embodiments of the present invention, a compact multi-UV-LED probe is provided for irradiating an object or sample under inspection.

In additional embodiments for the present invention, a compact catheter multi-UV-LED probe is provided for irradiating an object or sample under inspection.

In additional embodiments for the present invention, a compact catheter multi-UV-LED spectrometer system is provided for irradiating an object or sample under inspection.

The present invention provides a novel instrument with a variety of applications, including collecting "fingerprints" of multiple fluorescence spectra from a single material sample. Possible materials appropriate for such analysis include gem diamonds, paper, banknotes, forensic samples and biological materials.

It is proposed that a compact spectrometer be engineered that would allow the UV radiated by several (about six) such UV-emitting LEDs to be focused on a small specimen to allow multiple fluorescence spectra to be captured. Since the emitted light would be within the sensitivity range of silicon photo-detectors, the emitted spectrum from each UV wavelength could be captured simultaneously for all fluorescence wavelengths using a diffraction grating and a linear photo-detector array possibly comprising several thousand detectors. Such arrays are remarkably inexpensive since they are used in consumer-grade document and photograph scanners. Simultaneous capture of the emitted light allows the further dimension of after-glow data to be captured.

Additionally, the specimen can be chilled by means of a multi-stage Peltier cooler, providing yet another dimension for comparing and distinguishing material samples. Since the entire instrument could be made with no moving parts, it could be made as portable instrument at low cost. With multiple UV source wavelengths, multiple temperatures and a variety of delay periods to allow measurements of steady-state fluorescence as well as afterglow, hundreds of different spectra can be captured from a single sample in a few minutes. This large volume of measured data will facilitate the determination of similarity or dissimilarity between specimens with unprecedented statistical certainty.

The present invention provides a multi UV-LED probe system for detection of a characteristic of a sample, the system including a device comprising a probe head, the probe head including a plurality of UV-LEDs, an optic fiber bundle, an optional heating surface, an optional cooling surface and a light directing means adapted to transfer UV from the plurality of UV-LEDs to a region of the sample and further adapted to receive fluorescent light from the region to focus it into the optic fiber bundle and a power source adapted to provide electrical energy to the plurality of UV-LEDs, a spectrophotometer configured to receive the fluorescent light from the optic fiber bundle and a processor adapted to receive signals associated with the fluorescent light and to process the signals to provide the detection of the characteristic of the sample.

There is thus provided according to an embodiment of the present invention, a multi UV-LED probe system for providing a detection of a characteristic of a sample, the system including;

a. a device including a probe head, the probe head including;
  i. a plurality of UV-LEDs;
  ii. an optic fiber bundle; and
  iii. a light directing means adapted to transfer UV from the plurality of UV-LEDs to a region of the sample and further adapted to receive fluorescent light from the region to focus it into the optic fiber bundle; and
b. a power source adapted to provide electrical energy to the plurality of UV-LEDs;
c. a spectrophotometer configured to receive the fluorescent light from the optic fiber bundle; and
d. a processor adapted to receive signals associated with the fluorescent light and to process the signals to provide the detection of the characteristic of the sample.

Additionally, according to an embodiment of the present invention, the device is a catheter. Moreover, according to an embodiment of the present invention, the multi UV-LED probe system further includes a heating/cooling apparatus. Further, according to an embodiment of the present invention the sample is ex vivo, in vivo or in vitro.

Yet further, according to an embodiment of the present invention, the plurality of UV-LEDs includes at least six UV-LEDs.

Importantly, according to an embodiment of the present invention, the at least six UV-LEDs are each adapted to emit radiation in a wavelength range of 400 nm to 100 nm.

Yet further, according to an embodiment of the present invention, the at least six UV-LEDs are disposed symmetrically about a central axis of the probe head.

Additionally, according to an embodiment of the present invention, the optical fiber bundled is disposed through the central axis.

Furthermore, according to an embodiment of the present invention, the probe head further includes a light-directing means, disposed to receive radiation from the plurality of UV-LEDs and to focus the radiation on the sample.

Moreover, according to an embodiment of the present invention, the light-directing means is further adapted to focus fluorescent light from the sample to the optical fiber bundle.

Additionally, according to an embodiment of the present invention, the probe head further includes a heating surface and a cooling surface.

According to an additional embodiment of the present invention, the multi UV-LED probe system further includes a heating/cooling apparatus.

Further, according to an embodiment of the present invention, the heating surface and the cooling surface are in at least one of fluid connection and electrical connection with the heating/cooling apparatus.

Yet further, according to an embodiment of the present invention, at least one of the plurality of the UV-LEDs is adapted to irradiate UV at 240 nm, at 280 nm, at 290 nm, at 310 nm and at 325 nm on the sample.

There is thus provided according to another embodiment of the present invention, a method for optical detection of a characteristic of a sample, the method including;

a. irradiating a sample at multiple UV wavelengths;
b. detecting steady state fluorescence from the sample over a period of time; and
c. processing the steady state fluorescence over at least part of the period of time to detect the characteristic of the sample.

Additionally, according to an embodiment of the present invention, the irradiating step includes irradiating at 240 nm, 280 nm, 290 nm, 310 nm and 325 nm simultaneously.

Moreover, according to an embodiment of the present invention, the method is an endoscopic method.

Further, according to an embodiment of the present invention, the detecting step includes detecting hundreds of different spectra within a less than twenty minutes. Further, according to an embodiment of the present invention, the detecting step includes detecting hundreds of different spectra within a less than ten minutes. Moreover, according to an embodiment of the present invention, the detecting step includes detecting hundreds of different spectra within a less than five minutes.

Furthermore, according to an embodiment of the present invention, the detecting step further includes detecting an afterglow from the sample.

Additionally, according to an embodiment of the present invention, the detecting step includes detecting a first steady state fluorescence and a second steady state fluorescence from the sample. The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood. With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings.

DETAILED DESCRIPTION OF THE EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

Figure 1:
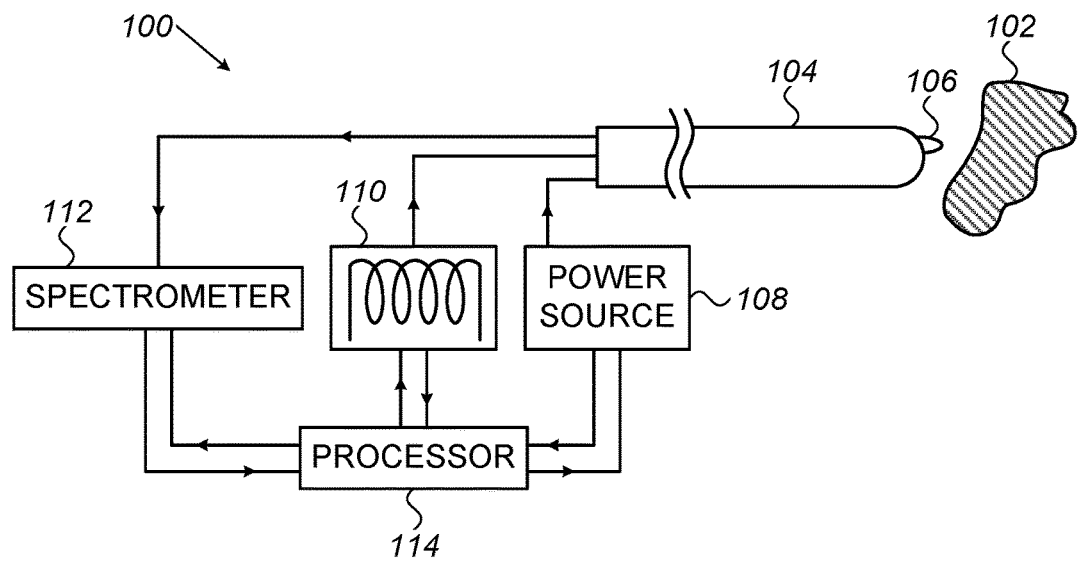
FIG. 1 is a simplified schematic illustration of a multi-UV-LED system for detection, in accordance with an embodiment of the present invention.

Reference is now made to FIG. 1, which is a simplified schematic illustration of a multi-UV-LED system 100 for detection, in accordance with an embodiment of the present invention.

System 100 comprises a device 104 having a device probe head 106. The device, may according to some embodiments, be a catheter. The probe head 106 is described in further detail with reference to FIGS. 2A-2B. The device receives electrical power from a power source 108. The power source may be controlled by a processor 114.

Optionally, system 100 comprises a heating/cooling apparatus 110, activated by the processor and configured to pass hot/cold fluid or electrical heating/cooling to the probe head.

The system comprises a spectrometer 112, configured to receive light energy from the probe head. The spectrometer is further configured to convert the light energy into electronic signals and to convey the signals to the processor for processing.

System 100 may be used, inter alia, to probe a sample 102. The sample may be disposed ex vivo, in vivo or in vitro detection.

Figure 2A:
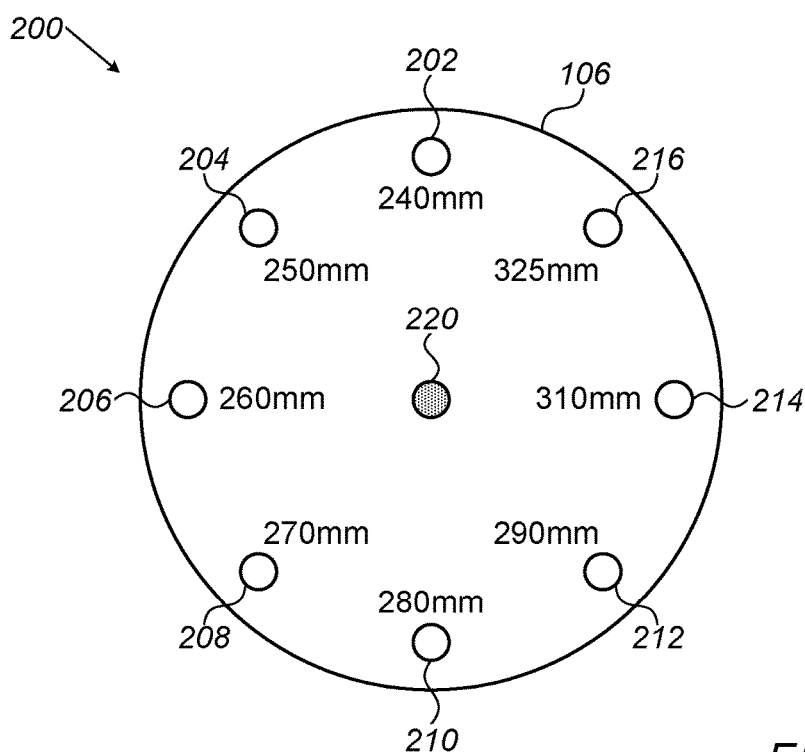
FIG. 2A is a simplified schematic illustration of a horizontal cross-section of a probe head of the system of FIG. 1, in accordance with an embodiment of the present invention.

FIG. 2A shows a simplified schematic illustration of a horizontal cross-section 200 of a probe head 106 of system 100 of FIG. 1, in accordance with an embodiment of the present invention. The probe head comprises a plurality of ultraviolet light emitting diodes (UV-LEDs), 202, 204, 206, 208, 212, 214 and 216. The wavelength of emission of each UV-LED may be similar or different. Each UV-LED emits UV light in the range of 400 nm to 100 nm. The number of UV-LEDs and their wavelength may vary according to the use and configuration of the probe. According to some embodiments, the UV-LEDs are disposed symmetrically about a central axis, through which an optical fiber bundle 220 is passed.

Figure 2B:
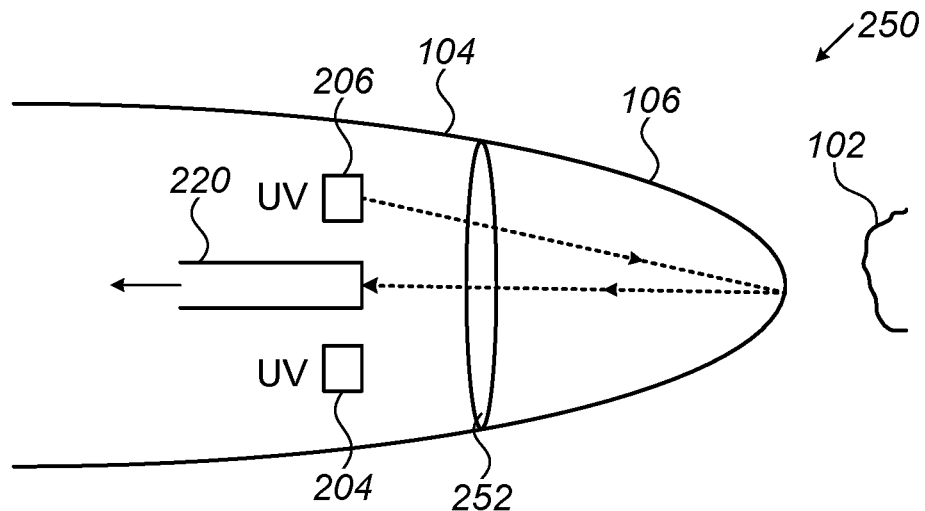
FIG. 2B is a simplified schematic illustration of a vertical cross-section of a probe head of the system of FIG. 1, in accordance with an embodiment of the present invention.

Turning to FIG. 2B, there is seen a simplified schematic illustration of a vertical cross-section 250 of a probe head of the system of FIG. 1, in accordance with an embodiment of the present invention. The probe head comprises a plurality of UV-LEDs 204, 206 and centrally disposed optical fiber bundle 220. The UV-LEDs and optical fiber bundle are disposed three dimensionally, such that UV light/radiation is radiated from the LEDs via a light directing means 252 to sample 102 or to an object (not shown). The light directing means is also adapted to focus fluorescent light from the sample to the optical fiber bundle.

Figure 3:
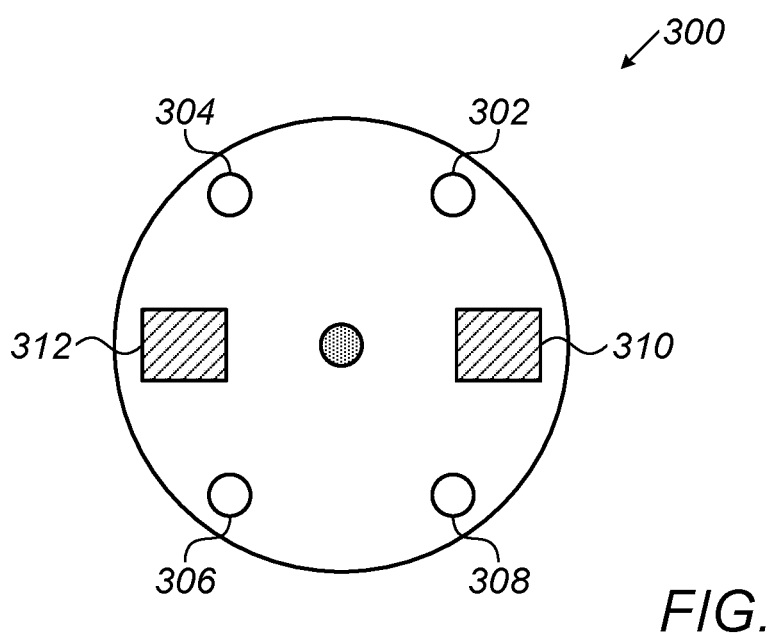
FIG. 3 is a simplified schematic illustration of a cross-section of a probe head of the system of FIG. 1, in accordance with an embodiment of the present invention.

FIG. 3 is another simplified schematic illustration of a cross-section 300 of a probe head of the system of FIG. 1, in accordance with an embodiment of the present invention. In this case, the probe head comprises a cooling element 310 and a heating element 312, connected to heating/cooling apparatus 110. The connection may electrical and/or fluid connection.

The probe head comprises a plurality of UV-LEDs 302, 304, 306, 308 and centrally disposed optical fiber bundle 320. The cooling/heating elements are adapted to cool/heat the sample or a part thereof, respectively.

Figure 4:
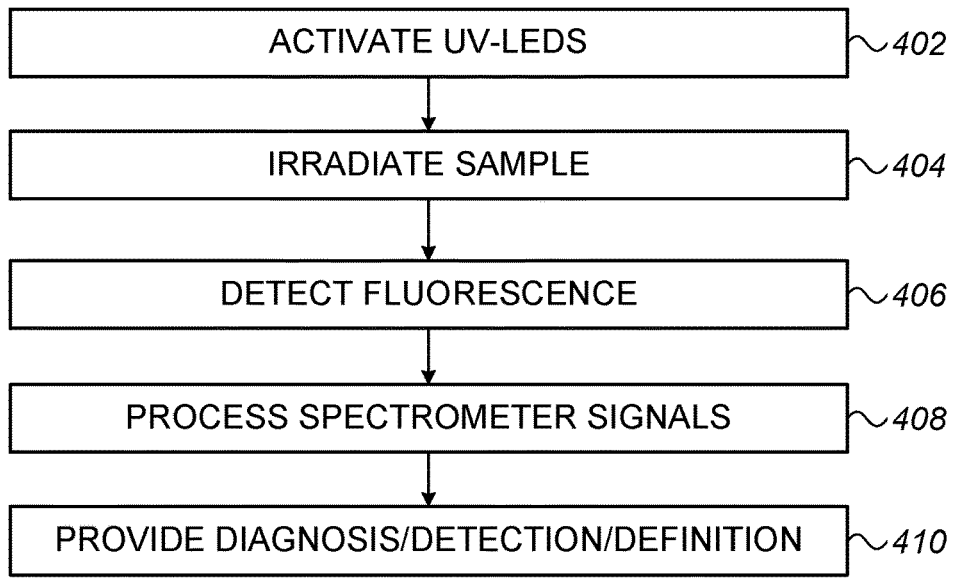
FIG. 4 is a simplified flow chart of a method of detection, in accordance with an embodiment of the present invention.

Reference is now made to FIG. 4, which is a simplified flow chart 400 of a method of detection, in accordance with an embodiment of the present invention.

In an activating UV-LEDs step 402, power source 108 is switched on and, it, in turn activates one or more UV-LEDs, 202, 204, 206, 208, 212, 214 and 216 (FIG. 2A) or 302, 304, 306 and 308 (FIG. 3). UV radiation passes through the light directing means and irradiates sample 102 in an irradiating sample step 404. For example, the sample may be irradiated at 240 nm, 280 nm, 290 nm, 310 nm and 325 nm simultaneously. This may occur in vivo, such as in an endoscopy. Certain parts of the sample may emit fluorescent light which is received by the light directing means 252 (FIG. 2B) and passed into the optic fiber bundle along the device and to the spectrophotometer 112 (FIG. 1). Hundreds of different spectra can be captured from the single sample in a few minutes. System 100 may comprise a diffraction grating and a linear photo-detector array possibly comprising several thousand detectors (not shown). The system is constructed and configured to capture steady state fluorescence from the sample in a detecting fluorescence step 406. This step may take from a few milliseconds to several hours. In some cases, it will take a few minutes.

Additionally or alternatively, the sample receives UV light or radiation and then a burst of infra-red light in an infra-red sample stimulating step (not shown). The sample emits fluorescent light responsive to at least one of the UV light and the infra-red light.

According to some embodiments, the sample exhibits the Gudden-Pohl effect (a light flash, which occurs when an electrical field is applied to a phosphor already excited by ultraviolet radiation).

Additionally or alternatively, the system is configured to capture a second steady state infra-red emission and/or other spectral emission. This may include an after-glow and/or a quenching effect, as are known in the art.

The processor (114, FIG. 1) is then operative to process signals from the spectrometer in a signal processing step 408 and to output a detection/diagnosis/definition in a detection outputting step 410. For example, certain cells within a colon may fluoresce differently to other cells, being indicative of inflammation, cancer, infection or disease.

Figure 5:
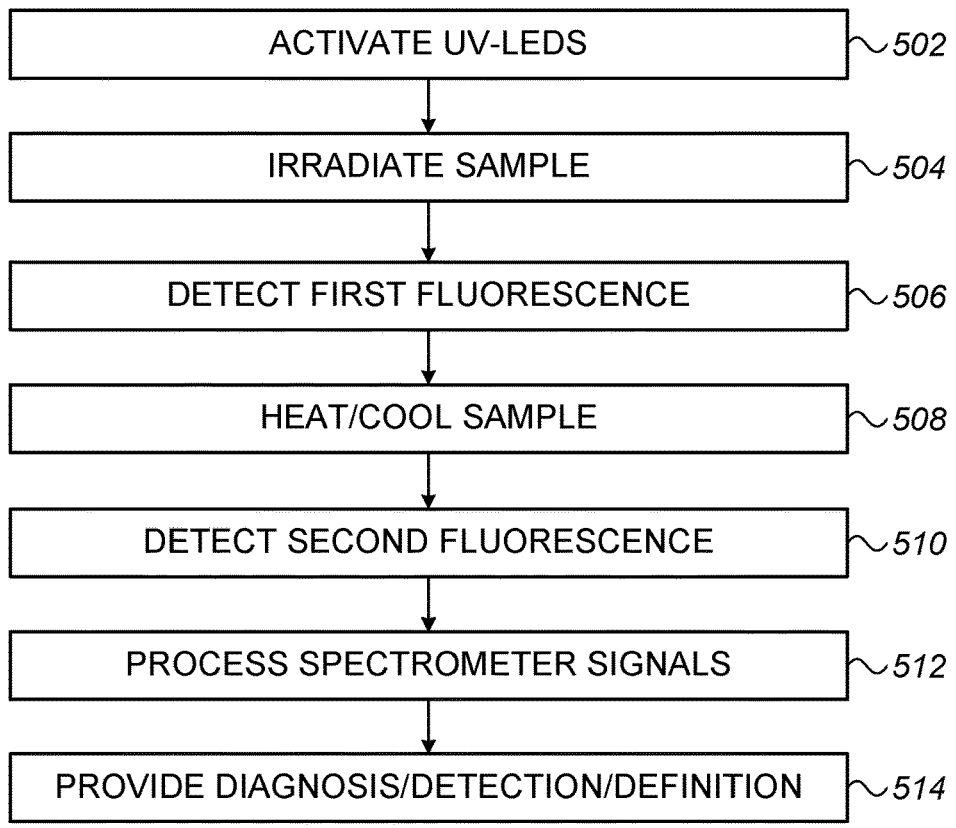
FIG. 5 is a simplified flow chart of another method of detection, in accordance with an embodiment of the present invention.

FIG. 5 is a simplified flow chart 500 of another method of detection, in accordance with an embodiment of the present invention.

In an activating UV-LEDs step 502, power source 108 is switched on and, it, in turn activates one or more UV-LEDs, 202, 204, 206, 208, 212, 214 and 216 (FIG. 2A) or 302, 304, 306 and 308 (FIG. 3). UV radiation passes through the light directing means and irradiates sample 102 in an irradiating sample step 504. For example, the sample may be irradiated at 240 nm, 280 nm, 290 nm, 310 nm and 325 nm simultaneously. This may occur in vivo, such as in an endoscopy. Certain parts of the sample may emit fluorescent light which is received by the light directing means 252 (FIG. 2B) and passed into the optic fiber bundle along the device and to the spectrophotometer 112 (FIG. 1). Hundreds of different spectra can be captured from the single sample in a few minutes. System 100 may comprise a diffraction grating and a linear photo-detector array possibly comprising several thousand detectors (not shown). The system is constructed and configured to capture steady state fluorescence from the sample in a detecting first fluorescence step 506. This step may take from a few milliseconds to several hours. In some cases, it will take a few minutes.

In a heating/cooling sample step 508, the heater/cooler is operative to pass hot/cold fluid along device or heating/cooling energy. The heating surface 312 or cooling surface 310 is brought into proximity or contact with the sample for a predetermined period of time, such as five seconds.

The system is constructed and configured to capture a second steady state fluorescence from the sample in a detecting second fluorescence step 510. Additionally or alternatively, the system is configured to capture a second steady state infra-red emission and/or other spectral emission. This may include an after-glow and/or a quenching effect, as are known in the art.

The processor (114, FIG. 1) is operative to process signals from the spectrometer in a signal processing step 512 (in parallel to and/or after steps 506, 508, 510) and to output a detection/diagnosis/definition in a detection outputting step 514. For example, certain cells within a colon may fluoresce differently to other cells, being indicative of inflammation, cancer, infection or disease.

Figure 6:
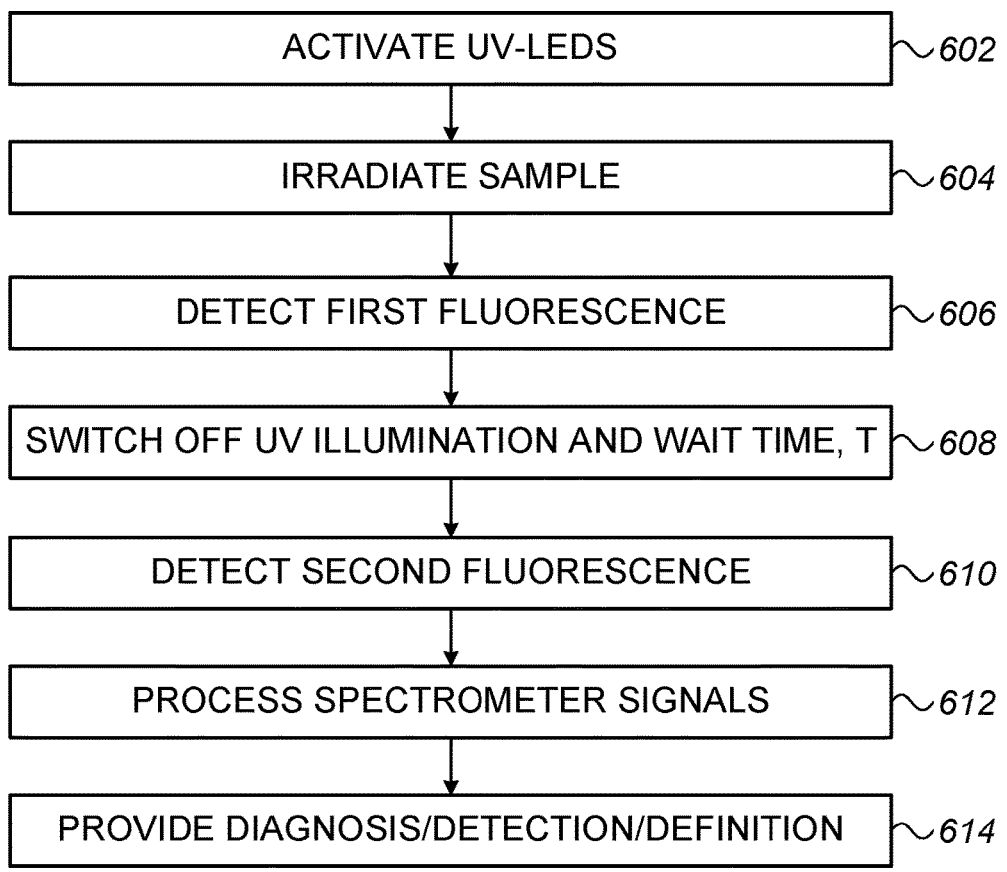
FIG. 6 is a simplified flow chart of another method of detection, in accordance with an embodiment of the present invention. In all the figures similar reference numerals identify similar parts.

FIG. 6 is a simplified flow chart of another method of detection, in accordance with an embodiment of the present invention;

In an activating UV-LEDs step 602, power source 108 is switched on and, it, in turn activates one or more UV-LEDs, 202, 204, 206, 208, 212, 214 and 216 (FIG. 2A) or 302, 304, 306 and 308 (FIG. 3). UV radiation passes through the light directing means and irradiates sample 102 in an irradiating sample step 604. For example, the sample may be irradiated at 240 nm, 280 nm, 290 nm, 310 nm and 325 nm simultaneously. This may occur in vivo, such as in an endoscopy. Certain parts of the sample may emit fluorescent light which is received by the light directing means 252 (FIG. 2B) and passed into the optic fiber bundle along the device and to the spectrophotometer 112 (FIG. 1). Hundreds of different spectra can be captured from the single sample in a few minutes. System 100 may comprise a diffraction grating and a linear photo-detector array possibly comprising several thousand detectors (not shown). The system is constructed and configured to capture steady state fluorescence from the sample in a detecting first fluorescence step 606. This step may take from a few milliseconds to several hours. In some cases, it will take a few minutes.

In a switching off UV illumination step 608, the power source (108, FIG. 1) is switched off. The sample may emit an afterglow. This step may include waiting for a predetermined period of time, such as twenty seconds.

The system is constructed and configured to capture a second steady state fluorescence from the sample in a detecting second fluorescence step 610. Additionally or alternatively, the system is configured to capture a second steady state infra-red emission and/or other spectral emission. This may include an after-glow and/or a quenching effect, as are known in the art. The example of a second fluorescent emission should not be deemed as limiting, but rather as exemplary.

The processor (114, FIG. 1) is operative to process signals from the spectrometer in a signal processing step 612 (in parallel to and/or after steps 606, 608, 610) and to output a detection/diagnosis/definition in a detection outputting step 614. For example, certain minerals within a rock sample may provide fluorescence and afterglow, which are indicative of the presence of a specific mineral, different to other parts of the rock.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. A multi UV-LED probe system for providing a detection of a characteristic of a sample, the system comprising:
    (a) a device comprising a probe head, the probe head comprising:
        a plurality of UV-LEDs;
        an optic fiber bundle;
        a light directing means adapted to transfer UV from said plurality of UV-LEDs to a region of said sample and further adapted to receive a first fluorescent light from said region to focus it into said optic fiber bundle;
        a heating surface;
        a cooling surface; and
    (b) a power source adapted to provide electrical energy to said plurality of UV-LEDs;
    (c) a heating and cooling apparatus in at least one of fluid connection and electrical connection with said heating surface and said cooling surface on said probe head;
    (d) a spectrophotometer configured to receive said fluorescent light from said optic fiber bundle; and
    (e) a processor adapted to receive signals associated with said fluorescent light and to process said signals to provide said detection of said characteristic of said sample.

2. A multi UV-LED probe system according to claim 1, wherein said device is a catheter.

3. A multi UV-LED probe system according to claim 1, wherein said heating and cooling apparatus is activated by said processor.

4. A multi UV-LED probe system according to claim 3, wherein said heating and cooling apparatus is further adapted to pass at least one of hot and cold fluid to said probe head.

5. A multi UV-LED probe system according to claim 4, wherein said probe heat further comprises a heating element and a cooling element.

6. A multi UV-LED probe system according to claim 5, wherein said system is configured to capture a second steady state fluorescence after a time delay after said first fluorescent light.

7. A multi UV-LED probe system according to claim 6, wherein said at least one of second steady state infra-red emission and other spectral emission is selected from the group consisting of an afterglow, a quenching effect and a Gudden-Pohl effect.

8. A multi UV-LED probe system according to claim 7, wherein at least one of said plurality of said UV-LEDs is adapted to irradiate UV at 240 nm, at 280 nm, at 290 nm, at 310 nm and at 325 nm on said sample.

9. A multi UV-LED probe system according to claim 1, wherein said sample is ex vivo, in vivo or in vitro.

10. A multi UV-LED probe system according to claim 1, wherein said plurality of UV-LEDs comprises at least six UV-LEDs.

11. A multi UV-LED probe system according to claim 10, wherein said at least six UV-LEDs are each adapted to emit radiation in a wavelength range of 400 nm to 100 nm.

12. A multi UV-LED probe system according to claim 10, wherein said at least six UV-LEDs are disposed symmetrically about a central axis of said probe head.

13. A multi UV-LED probe system according to claim 12, wherein said optical fiber bundled is disposed through said central axis.

14. A multi UV-LED probe system according to claim 13, wherein said probe head further comprises a light-directing means, disposed to receive radiation from said plurality of UV-LEDs and to focus said radiation on said sample.

15. A multi UV-LED probe system according to claim 14, wherein said light-directing means is further adapted to focus fluorescent light from the sample to the optical fiber bundle.

16. A multi UV-LED probe system according to claim 12, wherein said system is adapted to further capture at least one of second steady state infra-red emission and other spectral emission after said time delay.

17. A method for optical detection of a characteristic of a sample, the method comprising:
(a) irradiating a sample at multiple UV wavelengths;
(b) applying at least one of heating and cooling to said sample;
(c) detecting a first steady state fluorescence from said sample over a first period of time;
(d) waiting for a time delay;
(d) detecting a second steady state fluorescence from said sample over a second period of time; and
(e) processing said first steady state fluorescence and said second steady state fluorescence to detect said characteristic of said sample.

18. A method according to claim 17, wherein said irradiating step comprises irradiating at 240 nm, 280 nm, 290 nm, 310 nm and 325 nm simultaneously.

19. A method according to claim 17, wherein said method is an endoscopic method.

20. A method according to claim 17, wherein said detecting step comprises detecting hundreds of different spectra within a less than twenty minutes.

21. A method according to claim 20, wherein said detecting step further comprises detecting an afterglow from said sample.

22. A method according to claim 17, further comprising capture at least one of second steady state infra-red emission and other spectral emission after said time delay.

23. A method according to claim 22, wherein said at least one of second steady state infra-red emission and other spectral emission is selected from the group consisting of an afterglow, a quenching effect and a Gudden-Pohl effect.

* * * * *